United States Patent
Groza (10) Patent No.: US 11,631,482 B2
(45) Date of Patent: Apr. 18, 2023

(54) VISUALISING CLINICAL AND GENETIC DATA

(71) Applicant: GARVAN INSTITUTE OF MEDICAL RESEARCH, New South Wales (AU)

(72) Inventor: Tudor Groza, New South Wales (AU)

(73) Assignee: GARVAN INSTITUTE OF MEDICAL RESEARCH, New South Wales (AU)

( * ) Notice: Subject to any disclaimer, the term of this patent is extended or adjusted under 35 U.S.C. 154(b) by 450 days.

(21) Appl. No.: 16/979,005

(22) PCT Filed: Mar. 8, 2019

(86) PCT No.: PCT/AU2019/050208
§ 371 (c)(1),
(2) Date: Sep. 8, 2020

(87) PCT Pub. No.: WO2019/169452
PCT Pub. Date: Sep. 12, 2019

(65) Prior Publication Data
US 2021/0005298 A1  Jan. 7, 2021

(30) Foreign Application Priority Data

Mar. 9, 2018 (AU) .................................. 2018201712

(51) Int. Cl.
*G06F 3/0482* (2013.01)
*G06F 3/0484* (2022.01)
(Continued)

(52) U.S. Cl.
CPC ........... *G16H 15/00* (2018.01); *G06F 3/0482* (2013.01); *G06F 3/0484* (2013.01);
(Continued)

(58) Field of Classification Search
CPC .. G06F 3/0482; G06F 3/0484; G06F 16/9024; G06F 3/04842; G16B 20/20;
(Continued)

(56) References Cited

U.S. PATENT DOCUMENTS 8,024,128 B2 * 9/2011 Rabinowitz ............ G16H 50/70
703/2
10,431,331 B1 * 10/2019 Greenberg ............. G16H 40/63
(Continued)

FOREIGN PATENT DOCUMENTS

| WO | 2011/151500 | 12/2011 |
| WO | 2019/169452 | 9/2019 |

OTHER PUBLICATIONS

Amberger et al. (OMIM.org: Online Mendelian Inheritance in Man (OMIMR), an online catalog of human genes and genetic disorders), published Nov. 2014, pp. 1-10. (Year: 2014).*

(Continued)

*Primary Examiner* — Shahid K Khan
*Assistant Examiner* — Ahamed I Nazar
(74) *Attorney, Agent, or Firm* — Kilpatrick Townsend & Stockton LLP (57) ABSTRACT

This disclosure relates to generating interactive graphical visualisations of clinical and genetic data. A processor receives the clinical data indicative of observed phenotypes, accesses a database to determine associations of the observed phenotypes with disorders and accesses a second database to determine associations between the disorders and genetic properties. The processor then determines an association value for each combination of the observed phenotypes and the genetic properties based on a number of paths between them. The processor also generates a graphical user interface, comprising an arrangement of the association values and a user control element associated with the (Continued)

phenotypes and/or the genetic properties. Finally, upon detecting user interaction in relation to the user control element, the processor re-arranges the arrangement of the association values in the graphical user interface to reflect the detected user interaction.

15 Claims, 4 Drawing Sheets

(51) Int. Cl.

| | | |
|---|---|---|
| *G16H 15/00* | (2018.01) | |
| *G16H 70/60* | (2018.01) | |
| *G16H 10/60* | (2018.01) | |
| *G16H 50/70* | (2018.01) | |
| *G06F 16/901* | (2019.01) | |
| *G16B 45/00* | (2019.01) | |
| *G16B 20/00* | (2019.01) | |

(52) U.S. Cl.
CPC ......... *G06F 16/9024* (2019.01); *G16B 20/00* (2019.02); *G16B 45/00* (2019.02); *G16H 10/60* (2018.01); *G16H 50/70* (2018.01); *G16H 70/60* (2018.01)

(58) Field of Classification Search
CPC ........ G16B 20/40; G16B 20/30; G16B 45/00; G16H 50/20; G16H 10/60; G16H 50/00; G16H 50/30; G16H 50/50; G16H 50/70; G16H 50/80; G16H 70/60; G16H 70/00
See application file for complete search history.

(56) References Cited

U.S. PATENT DOCUMENTS

| | | | | |
|---|---|---|---|---|
| 10,450,611 | B2* | 10/2019 | West | G16B 20/10 |
| 2005/0192761 | A1* | 9/2005 | Jacob | G16B 20/20 |
| | | | | 702/19 |
| 2016/0154928 | A1* | 6/2016 | Zeskind | G16B 30/00 |
| | | | | 514/274 |
| 2016/0283484 | A1* | 9/2016 | Chandratillake | G06F 16/248 |
| 2017/0242959 | A1* | 8/2017 | Page | G16B 20/00 |
| 2017/0286594 | A1* | 10/2017 | Reid | G16B 20/40 |
| 2017/0351807 | A1* | 12/2017 | Shtir | G16B 20/00 |
| 2019/0333636 | A1* | 10/2019 | Bennett | G16H 50/00 |
| 2020/0167914 | A1* | 5/2020 | Stamatoyannopoulos | |
| | | | | G16B 40/20 |

OTHER PUBLICATIONS

Goh et al. (The human disease network), published Feb. 2007, pp. 1-6. (Year: 2007).*
Can, Mapping and Analysis of Human Disease Network Map (Diseasome) on Mouse Genotype & Phenotype Network, pp. 1-168, published Aug. 2017. (Year: 2017).*
Glueck et al. (PhenoBlocks: Phenotype Comparison Visualizations), published Jan. 2016, pp. 1-10. (Year: 2016).*
Glueck et al. (PhenoStacks: Cross-Sectional Cohort Phenotype Comparison Visualizations), published Jan. 2017, pp. 1-10. (Year: 2017).*
Peng et al. (A novel method to measure the semantic similarity of HPO terms), published Jan. 2017, pp. 1-10. (Year: 2017).*
WO2011151500A1—Arrangement and method for finding relationships among data, published Dec. 2011, pp. 1-29. (Year: 2011).*
International Application No. PCT/AU2019/050208, "International Sarch Report", dated Apr. 5, 2019, 4 pages.
International Application No. PCT/AU2019/050208, Written Opinion, dated Apr. 5, 2019, 5 pages.
Glueck et al., ""PhenoStacks: Cross-Sectional Cohort Phenotype Comparison Visualizations"", IEEE Transactions on Visualization and Computer Graphics, Institute of Electrical and Electronics Engineers,, 2016, 11 pages.
Hristovski et al., ""Using literature-based discovery to identify disease candidate genes"", International journal of medical informatics, 74.2-4,, 2005, pp. 289-298.

* cited by examiner

VISUALISING CLINICAL AND GENETIC DATA

RELATED APPLICATION

The present application is a National Stage Application filed under 35 U.S.C. § 371, of International Application No. PCT/AU2019/050208, entitled "Visualizing Clinical and Genetic Data" and filed Mar. 8, 2019, which claims priority to Australian application 2018201712, filed on Mar. 9, 2018. Each of these applications is incorporated herein by reference in its entirety and for all purposes.

TECHNICAL FIELD

This disclosure relates to generating interactive graphical visualisations of clinical and genetic data.

BACKGROUND

Clinicians generally examine patients and record their observations (phenotypes). Clinicians also have access to gene sequencing and to a stock of knowledge from specialists and researchers around the world. However, it is still difficult for clinicians to use this information efficiently. In particular, it is difficult for a clinician to decide which genes are relevant for the currently observed phenotype. That is, a clinician may want to find the genes that express the observed phenotype. In most cases, the phenotype is a qualitative trait but could also be a quantitative trait. For example, a clinician may want to create a personalised gene panel with genes that are relevant or that do potentially express the observed phenotype. Similarly, the clinician may want to analyse a whole genome sequencing (WGS) dataset but simply does not know where to look. There are too many genes that could potentially be relevant, which makes it difficult for the clinician to make an effective determination. In a similar context, the clinician may want to understand the biological processes. This means, the clinician does not only consider genes but biological processes and molecular functions. The ultimate aim may then be to decide on a treatment for the patient based on the observations. However, it is currently too difficult to do so due to the vast amount of data that is available.

For example, the Database Online Mendelian Inheritance in Man (OMIM) comprises about 7,500 disorders, which are annotated with phenotypes, where each disorder is associated with about 2-30 phenotypes and about 0-10 gene locations. For multiple observed phenotypes it therefore quickly becomes impossible to derive meaningful insights from this data.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY

There is a need for a computerised tool that the clinician can use and that provides access to the vast amount of data and knowledge that is available. This tool may filter the available options based on the observed phenotype so that the clinician can ultimately find a most relevant subset of genetic properties. This disclosure uses the term genetic properties to refer to genes as such (i.e. gene locations) as well as gene functions. Gene functions, in turn, may include molecular functions (molecular activities of gene products), cellular components (where gene products are active) and biological processes (pathways and larger processes made up of the activities of multiple gene products). However, this example may be expanded to more gene functions or a smaller subset of gene functions, such as biological processes only or any other component individually or in combination.

Disclosed herein is a method that quantifies the association between phenotypes and genes. A quantification allows the sorting of associated genes, which allows the reduction of data that is to be provided to a human user. This way, the human user is able to understand the data. For example, the quantification can be neatly displayed in a matrix of coloured boxes, which allows easy visual inspection of the different associations.

A method for creating an interactive graphical visualisation of clinical data comprises:

receiving the clinical data indicative of multiple observed phenotypes of a patient;

accessing a first database to determine first associations of each of the multiple observed phenotypes of the patient with multiple disorders;

accessing a second database to determine second associations between the multiple disorders and multiple genetic properties;

determining an association value for each combination of the multiple observed phenotypes and the multiple genetic properties based on a number of paths between that observed phenotype and that genetic property;

generating a graphical user interface on a computer system, comprising an arrangement of the association values for each of the genetic properties and each of the observed phenotypes, the graphical user interface further comprising a user control element associated with at least one of the multiple phenotypes and the multiple genetic properties;

monitoring user interaction in relation to the user control element and upon detecting user interaction in relation to the user control element, re-arranging the arrangement of the association values in the graphical user interface to reflect the detected user interaction.

It is an advantage that the method creates an arrangement of association values that is interactive in the sense that user interaction re-arranges the arrangement. This allows a clinician to more efficiently peruse the genetic properties for the particular patient for which the phenotypes have been observed. The method facilitates the identification of a personalised treatment by the clinician because the method assists the clinician in accessing and processing the available data in a meaningful way.

The method may further comprise determining a weight value for each path from a first observed phenotype over a first disorder to a first genetic property based on the number of observed phenotypes that are associated with the first disorder in the path and determining the association value based on the weight value.

Detecting the user interaction may comprise detecting user interaction in relation to one of the multiple genetic properties indicative of the user selecting the one of the multiple genetic properties and re-arranging the arrangement of the association values may comprise sorting the phenotypes by the association value for the selected genetic property.

Detecting the user interaction may comprise detecting user interaction in relation to one of the multiple observed phenotypes indicative of the user selecting the one of the multiple observed phenotypes and re-arranging the arrangement of the association values may comprise removing genetic properties that have no paths to the remaining observed phenotypes after removal of the observed phenotype selected by the user.

The arrangement of the association values may be a matrix of the observed phenotypes across genetic properties and a visual appearance of each field of the matrix is based on the association value associated with that field.

The visual appearance may comprise one of multiple predefined shadings indicative of a range of the association value.

The multiple genetic properties may comprise multiple gene locations and multiple gene functions. Accessing the second database may be to determine second associations between the multiple disorders and the multiple gene locations. The method may further comprise accessing a third database to determine third associations between the multiple gene locations and the multiple gene functions and determining the association value may be for each combination of the multiple observed phenotypes and the multiple gene functions based on a number of paths between that observed phenotype and that gene function.

The gene function may comprises one or more of:
molecular functions;
cellular components; and
biological processes.

The method may further comprise determining a weight value for each path from a first observed phenotype over a first disorder and a first gene location to a first gene function based on the number of paths from the first observed phenotype to the first gene location and determining the association value based on the weight value.

The method may further comprise normalising the weight value across the multiple gene locations.

The method may further comprise filtering the observed phenotypes by physiological system.

The method may further comprise displaying an indication of variants in whole genome sequencing data of the patient based on the association values for respective gene locations.

Accessing the first database or accessing the second database or both comprises accessing a graph database.

Software, when executed by a computer, causes the computer to perform the above method.

A computer system for creating an interactive graphical visualisation of clinical data comprises:
an input port to receive the clinical data indicative of multiple observed phenotypes of a patient;
a first database accessible to determine first associations of each of the multiple observed phenotypes of the patient with multiple disorders;
a second database accessible to determine second associations between the multiple disorders and multiple genetic properties;
a processor to:
determine an association value for each combination of the multiple observed phenotypes and the multiple genetic properties based on a number of paths between that observed phenotype and that genetic property;
generate a graphical user interface on a computer system, comprising an arrangement of the association values for each of the genetic properties and each of the observed phenotypes, the graphical user interface further comprising a user control element associated with at least one of the multiple phenotypes and the multiple genetic properties;
monitor user interaction in relation to the user control element and upon detecting user interaction in relation to the user control element, re-arranging the arrangement of the association values in the graphical user interface to reflect the detected user interaction; and
an output port to provide the graphical user interface to a user.

Optional features described of any aspect of method, computer readable medium or computer system, where appropriate, similarly apply to the other aspects also described here.

BRIEF DESCRIPTION OF DRAWINGS

An example will be described with reference to.

DESCRIPTION OF EMBODIMENTS

Figure 1:
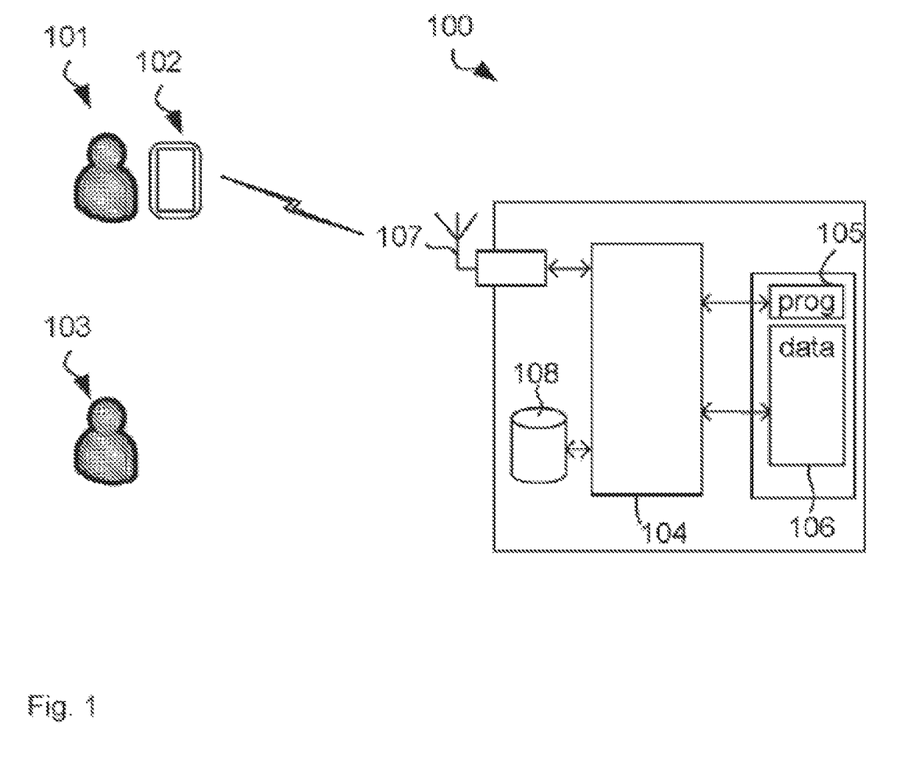
FIG. 1 illustrates a computer system for creating an interactive graphical visualisation of clinical data.

FIG. 1 illustrates a computer system 100 for creating an interactive graphical visualisation of clinical data. In one example, computer system 100 is a cloud-based computer system that is operated by clinician 101 with the use of a client device 102 such as a personal computer, tablet or other computing device. However, the proposed solution may equally be implemented locally. Clinician 101 examines a patient 103 and records clinical data into client device 102. The clinical data includes multiple phenotypes that clinician 101 observes in patient 103. It is noted that in this context phenotypes are not disorders but observations. Disorders on the other hand are conclusions that could be drawn based on the observed phenotypes.

The computer system 100 comprises a processor 104 connected to program memory 105, data memory 106, a communication port 107 and a database 108. When reference is made herein to a database, it is to be understood as any form of structured data storage including comma separated values, SQL or graph based databases, which are preferred due to their inherent ability to efficiently store and retrieve graph data as used herein.

The program memory 105 is a non-transitory computer readable medium, such as a hard drive, a solid state disk or CD-ROM. Software, that is, an executable program stored on program memory 105 causes the processor 104 to perform the method in FIG. 2, that is, processor 104 receives the clinical data from client device 102, accesses database 108, determines association values between observed phenotypes and genetic properties and finally creates an interactive display of these association values.

The processor 104 may then store the graphical user interface on data store 106, such as on RAM or a processor register. Processor 104 may also send the graphical user interface via communication port 107 to client device 102 such as through the use of a web server installed on computer system 100 and a browser application installed on client device 102.

The processor 104 may receive data, such as clinical data, from data memory 106 as well as from the communications port 107. In one example, the processor 104 receives clinical data from client device 102 via communications port 107, such as by using a Wi-Fi network according to IEEE 802.11. The Wi-Fi network may be a decentralised ad-hoc network, such that no dedicated management infrastructure, such as a router, is required or a centralised network with a router or access point managing the network.

In one example, processor 104 receives and processes the clinical data in real time. This means that the processor 104 creates the graphical user interface every time clinical data is received from client device 102 and completes this step before the client device 102 sends the next clinical data update. The same may apply for re-arranging the graphical user interface such that the time between the user interacting with the graphical user interface and the graphical user interface being updated on client device 102 is not perceived as a delay, such as less than 1 s or less than 100 ms.

Although communications port 107 is shown as distinct module, it is to be understood that any kind of data port may be used to receive data, such as a network connection, a memory interface, a pin of the chip package of processor 104, or logical ports, such as IP sockets or parameters of functions stored on data memory 106 and executed by processor 104. These parameters may be stored on data memory 106 and may be handled by-value or by-reference, that is, as a pointer, in the source code.

The processor 104 may receive data through all these interfaces, which includes memory access of volatile memory, such as cache or RAM, or non-volatile memory, such as an optical disk drive, hard disk drive, storage server or cloud storage. The computer system 100 may further be implemented within a cloud computing environment, such as a managed group of interconnected servers hosting a dynamic number of virtual machines.

It is to be understood that any receiving step may be preceded by the processor 104 determining or computing the data that is later received. For example, the processor 104 determines clinical data and stores the clinical data in data memory 106, such as RAM or a processor register. The processor 104 then requests the data from the data memory 106, such as by providing a read signal together with a memory address. The data memory 106 provides the data as a voltage signal on a physical bit line and the processor 104 receives the clinical data via a memory interface.

It is to be understood that throughout this disclosure unless stated otherwise, nodes, edges, graphs, solutions, variables, paths and the like refer to data structures, which are physically stored on data memory 106 or processed by processor 104. Further, for the sake of brevity when reference is made to particular variable names, such as "association value" or "number of paths" this is to be understood to refer to values of variables stored as physical data in computer system 100.

Figure 2:
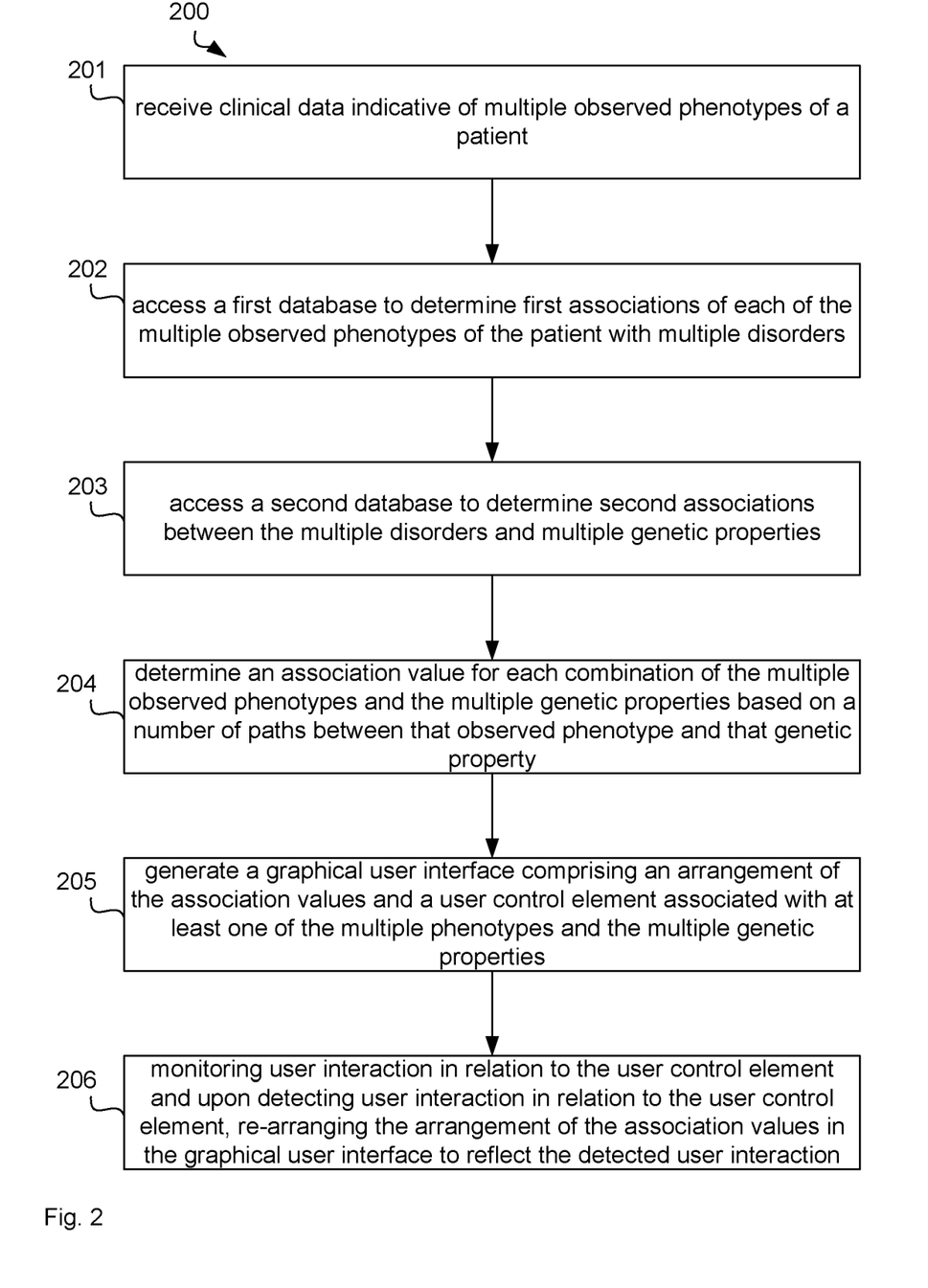
FIG. 2 illustrates a method for creating an interactive graphical visualisation of clinical data.

FIG. 2 illustrates a method 200 as performed by processor 104 for creating an interactive graphical visualisation of clinical data. FIG. 2 is to be understood as a blueprint for the software program and may be implemented step-by-step, such that each step in FIG. 2 is represented by a function in a programming language, such as C++ or Java. The resulting source code is then compiled and stored as computer executable instructions on program memory 105.

It is noted that for most humans performing the method 200 manually, that is, without the help of a computer, would be practically impossible. Therefore, the use of a computer is part of the substance of the invention and allows using the available data that would otherwise not be possible or prohibitively difficult due to the large amount of data and the large number of calculations that are involved.

Method 200 starts by processor 104 receiving 201 the clinical data from client device 102. The clinical data is indicative of multiple observed phenotypes of patient 103. In one example, clinician 101 enters observations as text in natural language and a natural language processor analyses the text input and maps it to a phenotype ontology, such as phenotypes included in OMIM or to the Human Phenotype Ontology (http://human-phenotype-ontology.github.io, HPO). As described on their website the HPO is a computational representation of a domain of knowledge based upon a controlled, standardized vocabulary for describing entities and the semantic relationships between them.

The HPO aims to provide a standardized vocabulary of phenotypic abnormalities encountered in human disease. Each term in the HPO describes a phenotypic abnormality, such as atrial septal defect. The HPO is currently being developed using the medical literature, Orphanet, DECIPHER, and OMIM. HPO currently contains approximately 11,000 terms (still growing) and over 115,000 annotations to hereditary diseases. The HPO also provides a large set of HPO annotations to approximately 4000 common diseases.

Processor 104 then accesses database 108 to determine first associations of each of the multiple observed phenotypes of the patient with multiple disorders. Again, OMIM can be used for this purpose. Processor 104 also accesses database 108 to determine second associations between the multiple disorders and multiple genetic properties, which can also be extracted from the OMIM database. It is noted that FIG. 1 shows an example of a local copy of database 108. In other examples, database 108 is hosted elsewhere and accessed by processor 104 via a database access protocol via the internet. This has the advantage that the local copy does not become outdated as the online version can be continuously curated.

Processor 104 further determines an association value for each combination of the multiple observed phenotypes and the multiple genetic properties. The association value is based on a number of paths between that observed phenotype and that genetic property.

Figure 3:
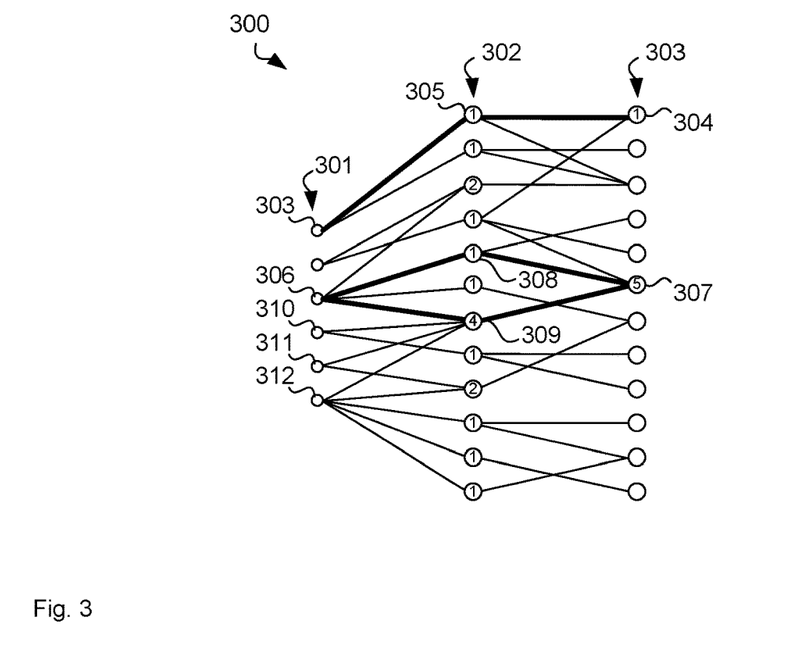
FIG. 3 illustrates an example graph comprising observed phenotypes disorders and genetic properties.

FIG. 3 illustrates an example graph 300 comprising a layer of observed phenotypes 301, a layer of disorders 302 and a layer of genetic properties 304. Each layer is understood to represent a subset of the nodes of the graph as shown in the figure. While FIG. 3 shows an example number of nodes and edges, it is to be understood that other applications comprise significantly more nodes in the disorder layer 302 and the genetic properties layer 303, such as more than 1,000 disorder nodes and more than 1,000 genetic properties for nodes layers 302 and 303. Without the help of the methods proposed herein, these numbers would lead to an overall number of different combinations that would be difficult, if not impossible, for humans to use. While clinician 101 is generally free to record as many observed phenotypes as desired, the number of phenotypes would generally be between 2 and 20 or more than 5.

Some example nodes in graph 300 are labelled for the following explanation on how to calculate the association value. Each association value is indicative of the association between one phenotype and one genetic property. As a result, for m phenotypes and n disorders there would be m times n association values. As mentioned above, the association value is based on the number of paths between a phenotype and a genetic property. For example, from first phenotype 303 to first genetic property 304 there is only a single path via first disorder 305, which is highlighted in FIG. 3 (nodes are counted from the top for easy of explanation). Therefore, the association value between first phenotype 303 and first genetic property 304 is 1. In contrast, from the third phenotype 306 to the sixth genetic property 307 there are two paths. One path is via fifth disorder 308 and one path is via seventh disorder 309. In one example, the number of paths (2) is the association value between the third phenotype 306 and the sixth genetic property 307. As mentioned above, graph databases, such as OrientDB would be beneficial as their use makes the determination of available paths computationally efficient compared to relational databases, such as SQL.

In a more sophisticated example, the association value is based on a weight value that is, in turn, based on the number of observed phenotypes that are associated with the first disorder in the path. This means that disorders that are associated with a large number of phenotypes carry a higher weight. Consequently, genetic properties that are linked to a phenotype via a disorder with a higher weight are considered to be stronger associated with that phenotype than with phenotypes to which the genetic property is linked via a disorder with a lower weight. In the graph of FIG. 3, this means that the weight of disorders 302 is based on the number of incident edges from phenotype layer 301. For example, first disorder 305 has one incident edge (from phenotype 303) while seventh disorder 309 has four incident edges (from phenotypes 306, 310, 311 and 312). In one example, the weight of the disorders is equal to the number of incident edges, that is, the weight of first disorder 305 is 1 and the weight for seventh disorder is 4. The other weights are provided in the nodes in FIG. 3. It is noted that the weights may also be calculated differently based on the number of associated phenotypes, such as a non-linear or polynomial function or based on cliques that the disorders form.

Processor 104 can then use the weights to calculate an association value for the genetic properties 304. Processor 104 may add the weight values for those disorder nodes that are connected to that genetic property. For example, for the association value between first phenotype 303 and first genetic property 304, processor adds only the weight value of the first disorder 305 resulting in an association value of 1, which is equal to the previous example. For the sixth genetic property 307, however, processor 104 adds the weight of fifth disorder 308 (1) to the weight of the seventh disorder 309 (4) and the result of the association value is 5. As can be appreciated now, this association value is significantly greater than in the previous example to reflect the fact that seventh disorder is associated with a large number of phenotypes. The resulting association values for this example are:

| Phenotype | G1 | G2 | G3 | G4 | G5 | G6 | G7 | G8 | G9 | G10 | G11 | G12 |
|---|---|---|---|---|---|---|---|---|---|---|---|---|
| P1 | 1 | 1 | 2 | 0 | 0 | 0 | 0 | 0 | 0 | 0 | 0 | 0 |
| P2 | 0 | 0 | 2 | 0 | 1 | 1 | 0 | 0 | 0 | 0 | 0 | 0 |
| P3 | 1 | 0 | 0 | 1 | 0 | 5 | 1 | 0 | 0 | 0 | 0 | 0 |
| P4 | 0 | 0 | 0 | 0 | 0 | 0 | 0 | 1 | 1 | 0 | 0 | 0 |
| P5 | 0 | 0 | 0 | 0 | 0 | 0 | 0 | 0 | 0 | 0 | 0 | 0 |
| P6 | 0 | 0 | 0 | 0 | 0 | 0 | 2 | 0 | 0 | 1 | 2 | 1 |

One example application in FIG. 3 is that the genetic properties 304 represent gene locations and processor 104 calculates associations between gene locations and observed phenotypes 301.

Figure 4:
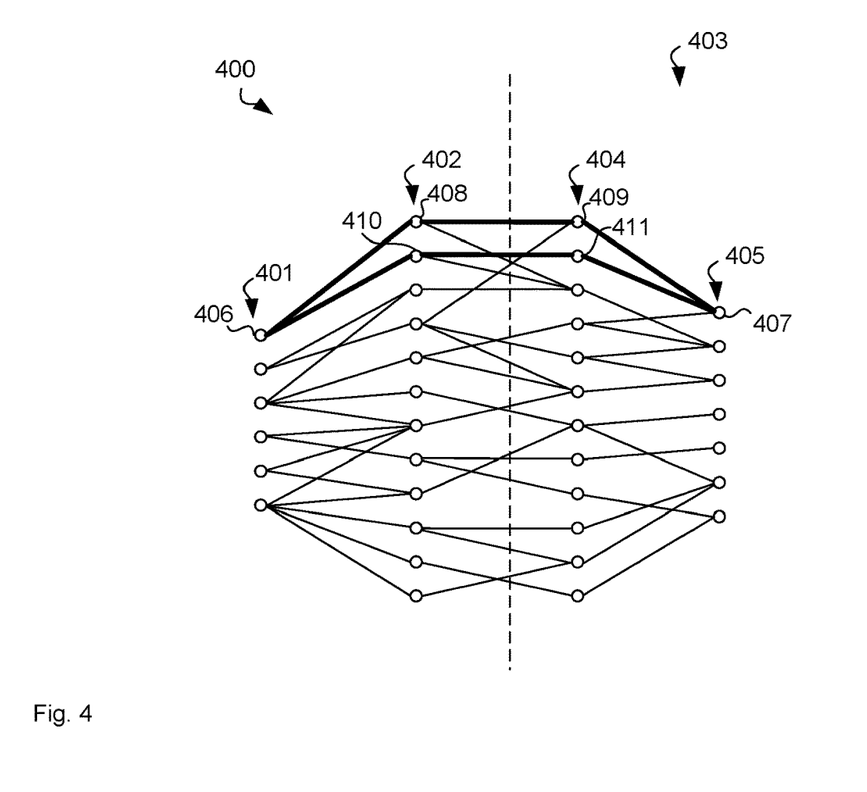
FIG. 4 illustrates an expansion of the graph in FIG. 3 by a gene functions layer.

FIG. 4 illustrates how the weight calculation can be expanded by a further layer. Again, FIG. 4 illustrates a graph 400 with an observed phenotypes layer 401, a disorders layer 402 and a genetic properties layer 403. In this example, however, the genetic properties layer 403 is partitioned into two further layers comprising a gene locations layer 404 and a gene functions layer 405. It is noted that in this example there are no edges (i.e. direct associations) between disorders and gene functions layer 405.

Processor 104 performs the same process that has been described above with reference to FIG. 3 to calculate association values between the phenotypes 401 and the gene locations 404, potentially using the weight values as also described above. Processor 104 may then normalise these association values, such as by determining the maximum association value of all nodes in layer 404 and dividing the association value by that maximum or by dividing the association value by a pre-determined maximum value. In any event, the resulting normalised association values are within a range of [0,1] but the un-normalised values may also be used. In this example, the maximum association value is 5 so processor 104 divides all association values by 5 resulting in the following values:

| Column1 | G1 | G2 | G3 | G4 | G5 | G6 | G7 | G8 | G9 | G10 | G11 | G12 |
|---|---|---|---|---|---|---|---|---|---|---|---|---|
| P1 | 0.2 | 0.2 | 0.4 | 0 | 0 | 0 | 0 | 0 | 0 | 0 | 0 | 0 |
| P2 | 0 | 0 | 0.4 | 0 | 0.2 | 0.2 | 0 | 0 | 0 | 0 | 0 | 0 |
| P3 | 0.2 | 0 | 0 | 0.2 | 0 | 1 | 0.2 | 0 | 0 | 0 | 0 | 0 |
| P4 | 0 | 0 | 0 | 0 | 0 | 0 | 0 | 0.2 | 0.2 | 0 | 0 | 0 |
| P5 | 0 | 0 | 0 | 0 | 0 | 0 | 0 | 0 | 0 | 0 | 0 | 0 |
| P6 | 0 | 0 | 0 | 0 | 0 | 0 | 0.4 | 0 | 0 | 0.2 | 0.4 | 0.2 |

Processor 104 now uses the association values calculated for gene locations 404 as weight values for the gene locations 404 similar to the weight values for disorders layer 402. That is, processor 104 calculates an association value between each phenotype and each gene function 405 by adding the weight values of each gene location node 404 that is in a path connecting to the respective phenotype to the corresponding gene function. For example, there are two paths from first phenotype 406 to first gene function 407, one path via first disorder 408 and first gene location 409 and another path via second disorder 410 and second gene location 411. As can be seen in the table above, the weight value (i.e. normalised association value) for first gene location 409 (from first phenotype) is 0.2 and for second gene location 411 is also 0.2. As a result, the association value between first phenotype and first gene function 407 is 0.2+0.2=0.4.

After processor 104 calculates an association value between each observer phenotype and each genetic property (being a gene location or gene function), processor 104 generates a graphical user interface on a computer system. This may involve generating a user interface on a screen directly connected to computer system 100 where the processor 104 performs the calculations. It may also involve generating the user interface in the form of web-accessible content, such as HTML and JavaScript. Client 102 can then access the web-accessible content and render the graphical user interface on a screen of client device 102. Various different front-end/back-end platforms may be used including an Angular/Flask framework.

Figure 5:
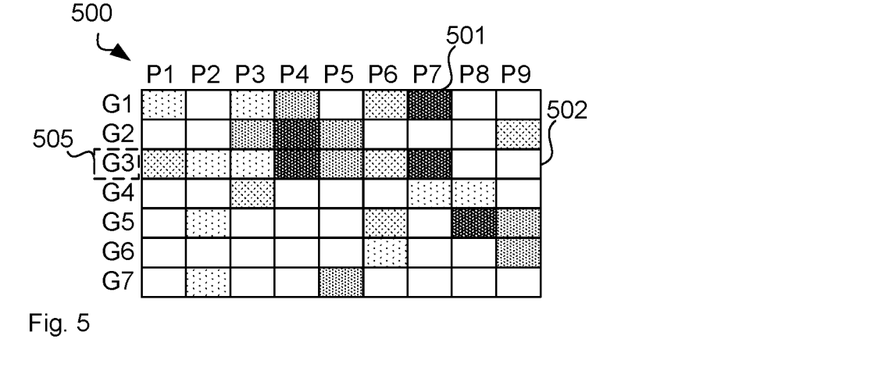
FIG. 5 illustrates a graphical user interface comprising an arrangement of the association values for each of the genetic properties and each of the observed phenotypes.

FIG. 5 illustrates a graphical user interface 500 comprising an arrangement of the association values for each of the genetic properties and each of the observed phenotypes (these are different to the association values provided above as they relate to a different example). In this example, the arrangement is a matrix of the observed phenotypes across genetic properties, that is, a grid of all possible combinations of observed phenotypes with genetic properties. In particular, each column represents one observed phenotype P1 to P9 and each row represents one genetic property G1 to G7. The visual appearance of each field of the matrix is defined by the shading of each field and is based on the association value associated with that field in the sense that greater association values have a darker shading and smaller association values have lighter shading. For example, field 501 has relatively dark shading indicating a relatively strong association between phenotype P7 and genetic property G1. On the other hand, field 502 has relatively light shading indicating a relatively weak association between observer phenotype P9 and genetic property G3. The shading of the fields may be selected from a predefined set of multiple shadings. For example, there may be only ten different shadings available that represent the entire range of association values so in case the association values are distributed between 0 and 1, the different shadings may each represent ranges of 0.1. This addresses the problem that it is generally difficult for humans to distinguish between similar shadings and the limited set of predefined shadings creates a coarser scale that makes it easier to distinguish shadings.

The matrix of fields which are shaded differently gives a clinician a useful visualisation of the associations and therefore, the underlying data. The clinician can readily determine which genetic properties are strongly associated with which observed phenotypes. As a result, the clinician can easily design a personalised gene panel for a sequencing order. Further, processor 104 may automatically access WGS data of patient 103 for the gene locations that have been identified and indicate to clinician 101 whether variants were called at those gene locations that are associated with the observed phenotypes. In effect, this provides an automatic navigation tool for clinician 101 to navigate the WGS data which would otherwise be too complicated.

Graphical user interface 500 further comprises a user control element 503, which is, in this example, associated with genetic property G3. However, it is noted that different phenotypes and different genetic properties may be associated with user control elements. In fact, each of the genetic properties and phenotypes may be associated with a separate user control element. The user control element effectively turns the associated genetic property or phenotype into a button for the user to click on. However, other control element such as drop-down lists or radio buttons may equally be used.

Processor 104 monitors user interaction in relation to the user control element, which again may be performed directly on computer system 100 or through JavaScript or other technologies to detect user interaction on client device 102. Upon detecting user interaction in relation to the user control element 503, processor 104 re-arranges the arrangement of the association values in the graphical user interface 500 to reflect the detected user interaction. Re-arranging the association values may comprises sorting, highlighting, selecting, de-selecting, removing and other operations.

In the example of FIG. 5 detecting the user interaction comprises detecting user interaction in relation to genetic property G3. This is indicative of the user selecting genetic property G3. In that example, re-arranging the arrangement of the association values comprises sorting the phenotypes P1 to P9 by the association value for the selected genetic property. As can be seen in FIG. 5, phenotypes P4 and P7 are strongly associated with G3 as indicated by their respective dark shading. Therefore, sorting the phenotypes by their association with G3 will sort P4 and P7 above the other phenotypes.

Figure 6:
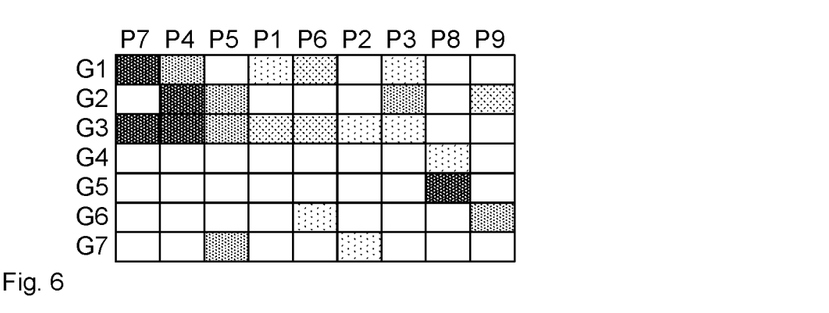
FIG. 6 illustrates a sorted version of FIG. 5.

FIG. 6 illustrates the result of sorting the phenotypes by their association with G3.

Figure 7:
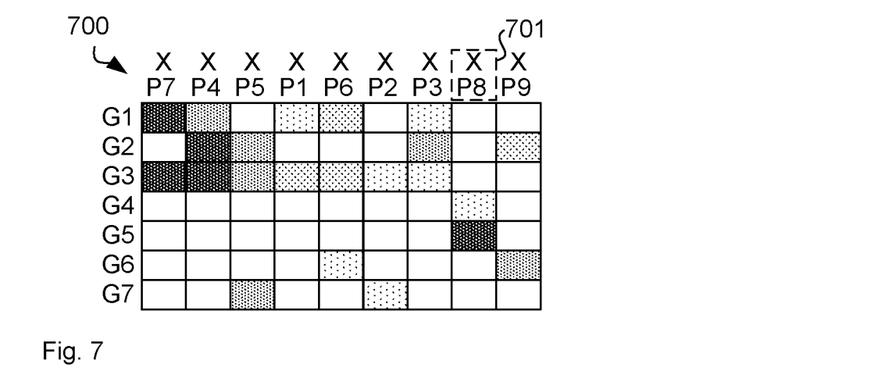
FIG. 7 illustrates a further user control element.

FIG. 7 illustrates a further example of a user interface 700 where a user control element 701 is associated with phenotype P8. Again, each phenotype may have a corresponding user control element associated with it. Accordingly, processor 104 detects user interaction in relation to observed phenotypes P8, which is indicative of the user selecting P8. Re-arranging the arrangement of the association values may then mean removing genetic properties that have no paths to the remaining observed phenotypes after removal of the observed phenotype P8 selected by the user. In the example of FIG. 7, phenotype P8 is associated with genetic properties G4 and G5. These genetic properties, in turn, are not associated to any of the other phenotypes. This means that the result of removing P8 is that G4 and G5 are not associated with any of the remaining phenotypes, that is, any of the phenotypes after removing the selected phenotype P8.

Figure 8:
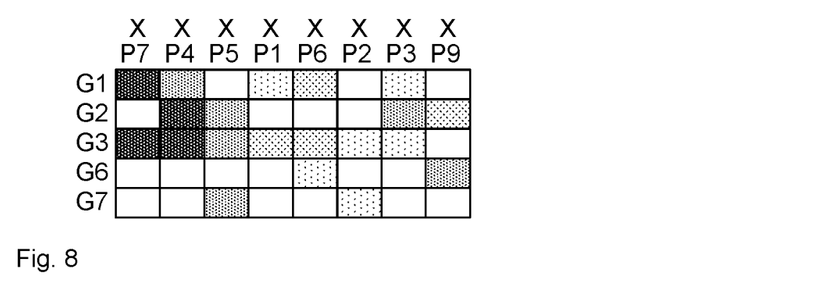
FIG. 8 illustrates the result of removing genetic properties.

FIG. 8 illustrates the result of removing genetic properties G4 and G5 as well as the selected phenotype P8. As can be seen, the matrix is already significantly reduced and conveniently re-ordered.

While the above examples relate to a matrix of observed phenotypes across genetic properties, it is noted that processor 104 may generate similar matrices of observed phenotypes across gene locations, gene functions, biological processes and others. In one example, processor 104 generates multiple matrices for a single patient, such as one matrix for observed phenotypes across gene locations, a second matrix for observed phenotypes across biological processes and a third matrix for observed phenotypes across molecular functions or cellular components. All other combinations are also envisaged.

In one example, processor 104 uses the association values as calculated above in all steps of representing the matrix as shown in FIGS. 5, 6, 7 and 8. In other examples, processor 104 re-calculates the association values when a phenotype is removed. This may change the association values because the number of phenotypes associated with a disorder defines the weight of that disorder in the graph (see FIG. 3) but for the sake of increased computation time, this inaccuracy could be ignored. In particular, such a re-computation could only result in a smaller set, which means that no results can be missed by not re-calculating the association values. In yet a further example, processor 104 may only perform necessary re-computations, that is, association values of genetic properties that are reachable in the graph starting from the removed phenotype.

In one example, the current disclosure uses the Gene Ontology (GO) from the Gene Ontology Consortium (geneontology.org). As described on their website at http://geneontology.org/page/ontology-documentation, the Gene Ontology defines the universe of concepts relating to gene functions ('GO terms'), and how these functions are related to each other ('relations'). It is constantly revised and expanded as biological knowledge accumulates. The GO describes function with respect to three aspects: molecular function (molecular-level activities performed by gene products), cellular component (the locations relative to cellular structures in which a gene product performs a function), and biological process (the larger processes, or 'biological programs' accomplished by multiple molecular activities).

The GO ontology is structured as a directed acyclic graph where each term has defined relationships to one or more other terms in the same domain, and sometimes to other domains. The GO vocabulary is designed to be species-agnostic, and includes terms applicable to prokaryotes and eukaryotes, and single and multicellular organisms.

In an example of GO annotation, the gene product "cytochrome c" can be described by the Molecular Function term "oxidoreductase activity", the Biological Process term "oxidative phosphorylation", and the Cellular Component terms "mitochondrial matrix" and "mitochondrial inner membrane".

In yet another example, the observed phenotypes, disorders and/or genetic properties are grouped by their physiological system, such as organ, cardiovascular, respiratory, immune, endocrine, digestive, nervous, renal, muscular, skeletal and reproductive systems. For example, they may be colour coded in the matrix. This way, clinician 101 can select one specific system for further analysis. For example, clinician 101 may see by looking at user interface 500 in FIG. 5 that the highest association values, or the only association values with a dark shading, fall into one particular physiological system. Clinician 101 can select that system and processor 104 filters the phenotypes, disorders or biological processes or other genetic properties by that system.

The value of these various filter steps is that a large number of genetic properties can be listed so that no genetic property is being missed. While this large number may be difficult to interpret by clinician 101, it is possible with the use of this disclosure for the clinician 101 to apply an intelligent filter to the output data to make the data suitable for human interpretation. A first filter may also filter out all results with an association value below a threshold that may be set by clinician 101 through the user interface. In an example workflow, clinician 101 first finds priority system, then proceeds to next level of biological processes. Clinician 101 will also be able to correlate the output on highly associated biological processes with family history.

While the above examples relate to positive association values, it is noted that negative values are also possible and that the absence of phenotypes in the observations can be considered.

Ontologies

Molecular Function

Molecular function terms describes activities that occur at the molecular level, such as "catalytic activity" or "binding activity". GO molecular function terms represent activities rather than the entities (molecules or complexes) that perform the actions, and do not specify where, when, or in what context the action takes place. Molecular functions generally correspond to activities that can be performed by individual gene products, but some activities are performed by assembled complexes of gene products. Examples of broad functional terms are "catalytic activity" and "transporter activity"; examples of narrower functional terms are "adenylate cyclase activity" or "Toll receptor binding".

It is easy to confuse a gene product name with its molecular function; for that reason GO molecular functions are often appended with the word "activity".

Cellular Component

These terms describe a location, relative to cellular compartments and structures, occupied by a macromolecular machine when it carries out a molecular function. There are two ways in which biologists describe locations of gene products: (1) relative to cellular structures (e.g., cytoplasmic side of plasma membrane) or compartments (e.g., mitochondrion), and (2) the stable macromolecular complexes of which they are parts (e.g., the ribosome). Unlike the other aspects of GO, cellular component concepts refer not to processes but rather a cellular anatomy.

Biological Process

A biological process term describes a series of events accomplished by one or more organized assemblies of molecular functions. Examples of broad biological process terms are "cellular physiological process" or "signal transduction". Examples of more specific terms are "pyrimidine metabolic process" or "alpha-glucoside transport". The general rule to assist in distinguishing between a biological process and a molecular function is that a process must have more than one distinct steps.

It will be appreciated by persons skilled in the art that numerous variations and/or modifications may be made to the specific embodiments without departing from the scope as defined in the claims.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "estimating" or "processing" or "computing" or "calculating", "optimizing" or "determining" or "displaying" or "maximising" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

The present embodiments are, therefore, to be considered in all respects as illustrative and not restrictive.

The invention claimed is:

1. A method for creating an interactive graphical visualisation of clinical data, the method comprising:
   receiving clinical data indicative of multiple observed phenotypes of a patient;
   accessing a first database to determine first associations of each of the multiple observed phenotypes of the patient with multiple disorders;
   accessing a second database to determine second associations between the multiple disorders and multiple genetic properties;
   determining an association value for each combination of the multiple observed phenotypes and the multiple genetic properties, wherein the association value for a combination is determined based on a number of paths between an observed phenotype and a genetic property;
   generating a graphical user interface on a computer system, comprising an arrangement of the association values for each of the genetic properties and each of the observed phenotypes, the graphical user interface further comprising a user control element associated with at least one of the multiple observed phenotypes and the multiple genetic properties;
   monitoring user interaction in relation to the user control element; and
   upon detecting user interaction in relation to the user control element, re-arranging the arrangement of the association values in the graphical user interface to reflect the detected user interaction.

2. The method of claim 1, further comprising determining a weight value for each path from a first observed phenotype over a first disorder to a first genetic property based on a number of observed phenotypes that are associated with the first disorder in the path and determining the association value based on the weight value.

3. The method of claim 1, wherein detecting the user interaction comprises detecting user interaction in relation to one of the multiple genetic properties indicative of a user selecting the one of the multiple genetic properties, and wherein re-arranging the arrangement of the association values comprises sorting the multiple observed phenotypes by the association value for the selected genetic property.

4. The method of claim 1, wherein detecting the user interaction comprises detecting user interaction in relation to one of the multiple observed phenotypes indicative of a user selecting the one of the multiple observed phenotypes, and wherein re-arranging the arrangement of the association values comprises removing genetic properties that have no paths to one or more remaining observed phenotypes after removal of the observed phenotype selected by the user.

5. The method of claim 1, wherein the arrangement of the association values is a matrix of at least one of the multiple observed phenotypes across genetic properties and a visual appearance of each field of the matrix is based on the association value associated with that field.

6. The method of claim 5, wherein the visual appearance comprises one of multiple predefined shadings indicative of a range of the association value.

7. The method of claim 1, wherein:
   the multiple genetic properties comprise multiple gene locations and multiple gene functions;
   accessing the second database is to determine second associations between the multiple disorders and the multiple gene locations;
   the method further comprises accessing a third database to determine third associations between the multiple gene locations and the multiple gene functions; and
   the association value for each combination of the multiple observed phenotypes and the multiple gene functions is further based on a number of paths between an observed phenotype and a corresponding gene function.

8. The method of claim 7, wherein at least one of the multiple gene functions comprises one or more of:
   molecular functions;
   cellular components; and
   biological processes.

9. The method of claim 7, further comprising determining a weight value for each path from a first observed phenotype over a first disorder and a first gene location to a first gene function based on the number of paths from the first observed phenotype to the first gene location and determining the association value based on the weight value.

10. The method of claim 9, further comprising normalising the weight value across the multiple gene locations.

11. The method of claim 1, further comprising filtering at least one the multiple observed phenotypes by physiological system.

12. The method of claim 1, further comprising displaying an indication of variants in whole genome sequencing data of the patient based on the association values for respective gene locations.

13. The method of claim 1, wherein accessing the first database or accessing the second database or both comprises accessing a graph database.

14. A non-volatile computer-readable medium with software code stored thereon that, when executed by a computer, causes the computer to perform one or more actions comprising:
   receiving clinical data indicative of multiple observed phenotypes of a patient;
   accessing a first database to determine first associations of each of the multiple observed phenotypes of the patient with multiple disorders;
   accessing a second database to determine second associations between the multiple disorders and multiple genetic properties;
   determining an association value for each combination of the multiple observed phenotypes and the multiple genetic properties, wherein the association value for a combination is determined based on a number of paths between an observed phenotype and a genetic property;
   generating a graphical user interface on a computer system, comprising an arrangement of the association values for each of the genetic properties and each of the observed phenotypes, the graphical user interface further comprising a user control element associated with at least one of the multiple observed phenotypes and the multiple genetic properties;
   monitoring user interaction in relation to the user control element; and
   upon detecting user interaction in relation to the user control element, re-arranging the arrangement of the association values in the graphical user interface to reflect the detected user interaction.

15. A computer system for creating an interactive graphical visualisation of clinical data, the computer system comprising:
- an input port to receive clinical data indicative of multiple observed phenotypes of a patient;
- a first database accessible to determine first associations of each of the multiple observed phenotypes of the patient with multiple disorders;
- a second database accessible to determine second associations between the multiple disorders and multiple genetic properties;
- a processor to:
  - determine an association value for each combination of the multiple observed phenotypes and the multiple genetic properties, wherein the association value for a combination is based on a number of paths between an observed phenotype and a genetic property;
  - generate a graphical user interface on a computer system, comprising an arrangement of the association values for each of the genetic properties and each of the observed phenotypes, the graphical user interface further comprising a user control element associated with at least one of the multiple observed phenotypes and the multiple genetic properties;
  - monitor user interaction in relation to the user control element; and
  - upon detecting user interaction in relation to the user control element, re-arrange the arrangement of the association values in the graphical user interface to reflect the detected user interaction; and
- an output port to provide the graphical user interface to a user.

* * * * *

UNITED STATES PATENT AND TRADEMARK OFFICE
CERTIFICATE OF CORRECTION

| | | |
|---|---|---|
| PATENT NO. | : 11,631,482 B2 | Page 1 of 1 |
| APPLICATION NO. | : 16/979005 | |
| DATED | : April 18, 2023 | |
| INVENTOR(S) | : Tudor Groza | |

It is certified that error appears in the above-identified patent and that said Letters Patent is hereby corrected as shown below:

On the Title Page

(73) Assignee:, the name and location of the assignee reading "GARVAN INSTITUTE OF MEDICAL RESEARCH, New South Wales (AU)" should read "PRYZM HEALTH IQ PTY LTD, Southport (AU)"

Signed and Sealed this
Twenty-ninth Day of April, 2025

Coke Morgan Stewart
*Acting Director of the United States Patent and Trademark Office*